(12) United States Patent
Marik et al.

(10) Patent No.: US 8,617,215 B2
(45) Date of Patent: Dec. 31, 2013

(54) CONNECTING ELEMENT AND SYSTEM FOR FLEXIBLE SPINAL STABILIZATION

(75) Inventors: Greg C. Marik, Collierville, TN (US);
Carlos E. Gil, Memphis, TN (US);
Henry Keith Bonin, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1116 days.

(21) Appl. No.: 12/120,573

(22) Filed: May 14, 2008

(65) Prior Publication Data

US 2009/0287252 A1 Nov. 19, 2009

(51) Int. Cl.
*A61B 17/70* (2006.01)

(52) U.S. Cl.
USPC .......................................... 606/257

(58) Field of Classification Search
USPC ........... 606/60, 246, 254–255, 257, 259, 260, 606/263, 264–278
See application file for complete search history.

(56) References Cited

U.S. PATENT DOCUMENTS

| | | |
|---|---|---|
| 5,375,823 A | 12/1994 | Navas |
| 5,540,688 A | 7/1996 | Navas |
| 6,241,730 B1 | 6/2001 | Alby |
| 2003/0009226 A1 | 1/2003 | Graf |
| 2004/0243239 A1 | 12/2004 | Taylor |
| 2005/0065514 A1* | 3/2005 | Studer .............................. 606/61 |
| 2005/0171540 A1 | 8/2005 | Lim et al. |
| 2005/0203519 A1 | 9/2005 | Harms et al. |
| 2005/0261685 A1 | 11/2005 | Fortin et al. |
| 2006/0129239 A1 | 6/2006 | Kwak |
| 2006/0142758 A1 | 6/2006 | Petit |
| 2006/0149238 A1* | 7/2006 | Sherman et al. ................. 606/61 |
| 2006/0189985 A1 | 8/2006 | Lewis |
| 2006/0264937 A1 | 11/2006 | White |
| 2007/0233064 A1 | 10/2007 | Holt |
| 2007/0270814 A1 | 11/2007 | Lim et al. |
| 2007/0270837 A1* | 11/2007 | Eckhardt et al. ................. 606/61 |
| 2007/0270838 A1* | 11/2007 | Bruneau et al. ................. 606/61 |
| 2008/0058812 A1* | 3/2008 | Zehnder .......................... 606/61 |
| 2008/0140076 A1* | 6/2008 | Jackson .......................... 606/60 |
| 2008/0147122 A1* | 6/2008 | Jackson ......................... 606/246 |
| 2008/0154308 A1* | 6/2008 | Sherman et al. .............. 606/265 |
| 2008/0172091 A1* | 7/2008 | Anderson ..................... 606/246 |
| 2008/0294198 A1* | 11/2008 | Jackson ......................... 606/246 |
| 2008/0300633 A1* | 12/2008 | Jackson ......................... 606/257 |
| 2009/0093846 A1* | 4/2009 | Hestad .......................... 606/255 |
| 2009/0240286 A1* | 9/2009 | Friedrich et al. .............. 606/255 |
| 2009/0275986 A1* | 11/2009 | Prevost et al. ................. 606/278 |
| 2009/0299411 A1* | 12/2009 | Laskowitz et al. ............ 606/246 |
| 2010/0004685 A1* | 1/2010 | Justis et al. ................... 606/246 |
| 2010/0010542 A1* | 1/2010 | Jackson ......................... 606/254 |

* cited by examiner

*Primary Examiner* — Eduardo C Robert
*Assistant Examiner* — Michelle C Eckman

(57) ABSTRACT

An elongated connecting element and system for dynamic spinal stabilization is disclosed. The connecting element and system provides for resistance to shear forces applied to the connecting element as well as provides for rotational stability of a resilient intermediate element disposed between two end members.

20 Claims, 7 Drawing Sheets

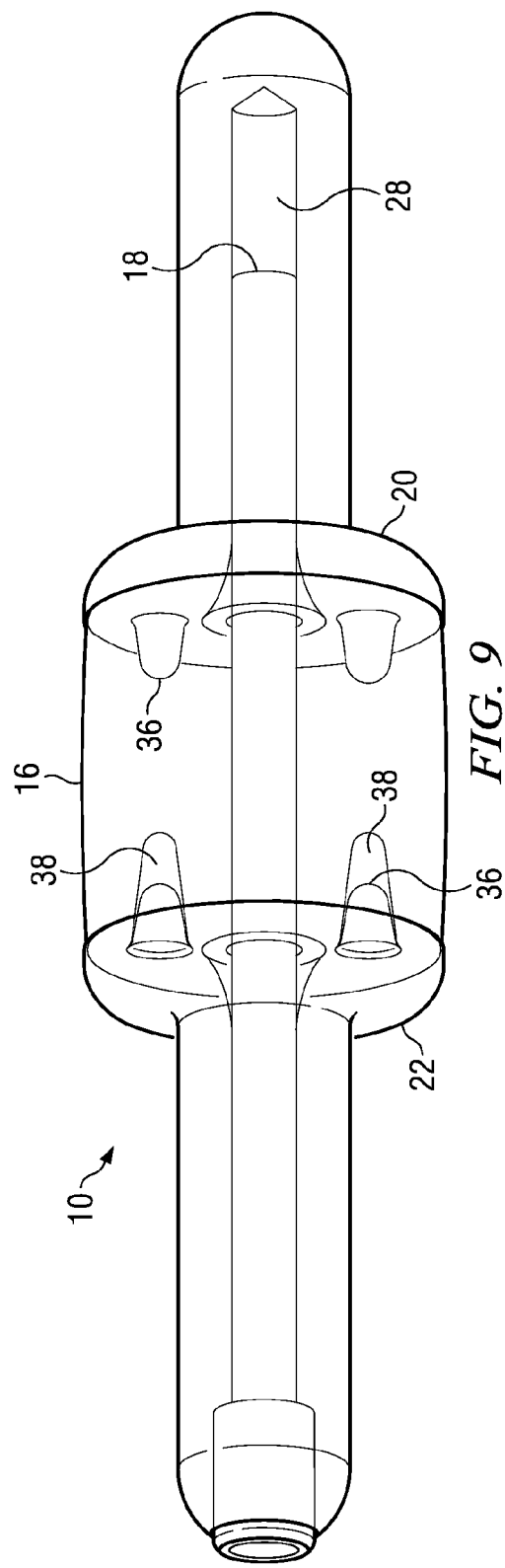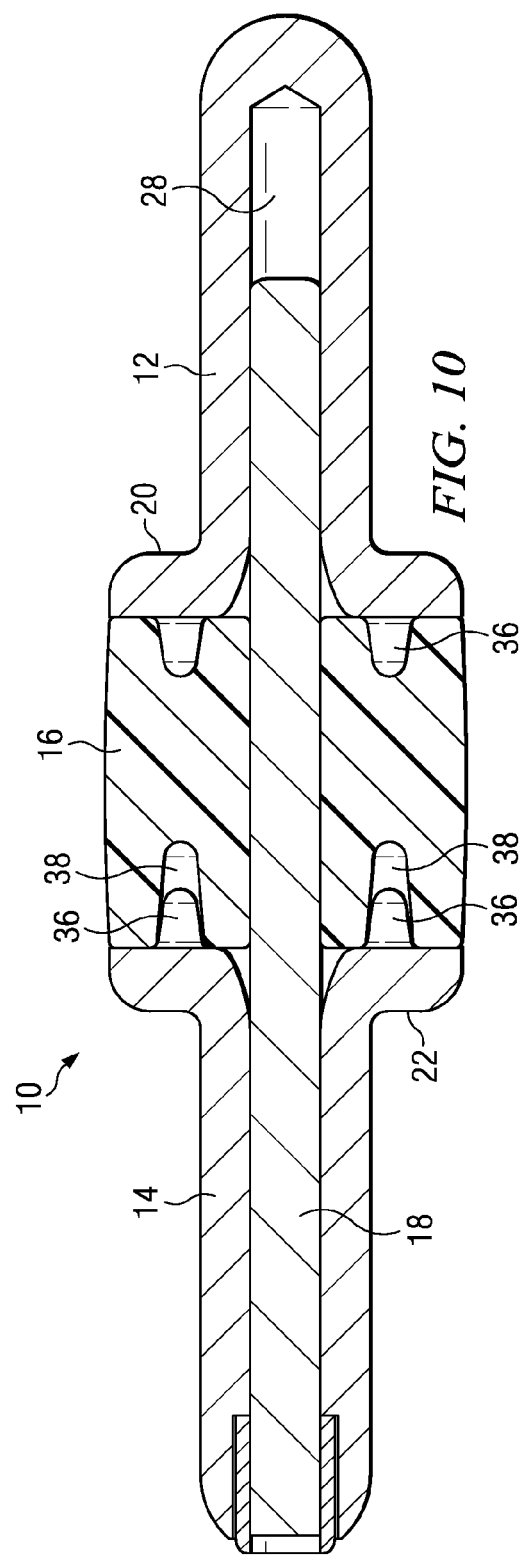

CONNECTING ELEMENT AND SYSTEM FOR FLEXIBLE SPINAL STABILIZATION

BACKGROUND

Elongated connecting elements, such as rods, plates, tethers, wires, cables, and other devices have been implanted along the spinal column and connected between two or more anchors engaged between one or more spinal motion segments. Some connecting elements provide a rigid construct that resists movement of the spinal motion segment in response to spinal loading or movement of the spinal motion segment by the patient. Still other connecting elements are flexible to permit at least limited spinal motion while providing resistance to loading and motion of the spinal motion segment. Such flexible connecting elements can be considered to provide dynamic spinal stabilization since at least limited movement of the spinal motion segment is preserved after implantation of the connecting element.

While prior connecting elements provide various spinal stabilization options, there remains a need for connecting elements that can provide dynamic resistance to shear forces and permit motion of the spinal column segment in different directions while maintaining stabilization of the spinal column segment and the structural integrity of the connecting element.

SUMMARY

The present invention generally relates to devices and methods for dynamically stabilizing a spinal column motion segment including at least two vertebrae by engaging an elongated connecting element between the two vertebrae. An exemplary connecting element includes a pair of end members and a resilient intermediate element positioned between and flexibly connecting the end members to one another.

In one aspect a spinal stabilization system for stabilizing one vertebral body with respect to a second vertebral body includes first and second anchor assemblies attachable to respective ones of first and second vertebral bodies and an elongated connecting element including opposite first and second end members and having a length along a longitudinal axis between the first and second end members sized for positioning between and engaging each of the first and second anchor assemblies when the first and second anchor assemblies are attached to the respective vertebral bodies. Each of the first and second end members includes a flange and a perpendicularly extending cylindrical wall portion extending from the perimeter of the respective flange along the longitudinal axis creating a cup shape. The connecting element further includes a resilient intermediate element within and between the cup-shaped flanges of the first and second end members and a flexible tether extending between the first and second end members and through the resilient intermediate member along the longitudinal axis, such as within axial bores of each of the first end second end members.

In another aspect, a spinal stabilization system for stabilizing one vertebral body with respect to a second vertebral body includes first and second anchor assemblies attachable to respective ones of first and second vertebral bodies and an elongated connecting element including opposite first and second end members and having a length along a longitudinal axis between the first and second end members sized for positioning between and engaging each of the first and second anchor assemblies when the first and second anchor assemblies are engaged to the respective vertebral bodies. Each of the first and second end members includes a flange having at least one protuberance extending therefrom. The connecting element further includes a resilient intermediate element positioned between the end members and having a plurality of indentations configured to cooperate with the protuberances. The connecting element further includes a flexible tether extending between the first and second end members and through the resilient intermediate member along the longitudinal axis, such as within axial bores of each of the first end second end members.

In a further aspect, a connecting element for stabilizing one vertebral body with respect to a second vertebral body in a dynamic spinal stabilization system includes an elongated body extending along a longitudinal axis that includes opposite first and second end members and a resilient intermediate element between and flexibly supporting the first and second end members. Each of the first and second end members includes a flange and a perpendicularly extending cylindrical wall portion extending from the perimeter of the respective flange along the longitudinal axis creating a cup shape. The connecting element further includes a resilient intermediate element within and between the cup-shaped flanges of the first and second end members. The connecting element further includes a flexible tether extending between the first and second end members and through the resilient intermediate element along the longitudinal axis, such as within axial bores of each of the first end second end members.

In yet another aspect, a connecting element for stabilizing one vertebral body with respect to a second vertebral body in a dynamic spinal stabilization system includes an elongated body extending along a longitudinal axis that includes opposite first and second end members and a resilient intermediate element between and flexibly supporting the first and second end members. Each of the first and second end members includes a flange having at least one protuberance extending therefrom. The connecting element further includes a resilient intermediate element positioned between the end members and having a plurality of indentations configured to cooperate with the protuberances. The connecting element further includes a flexible tether extending between the first and second end members and through the resilient intermediate element along the longitudinal axis, such as within axial bores of each of the first and second end members.

These and other aspects are described below.

BRIEF DESCRIPTION OF THE DRAWINGS

FIG. 9 is a phantom perspective view of the elongated connecting element embodiment of FIG. 8.

FIG. 10 is a cross-sectional view of the elongated connecting element embodiment of FIG. 8.

DESCRIPTION OF THE ILLUSTRATED EMBODIMENTS

Figure 1:
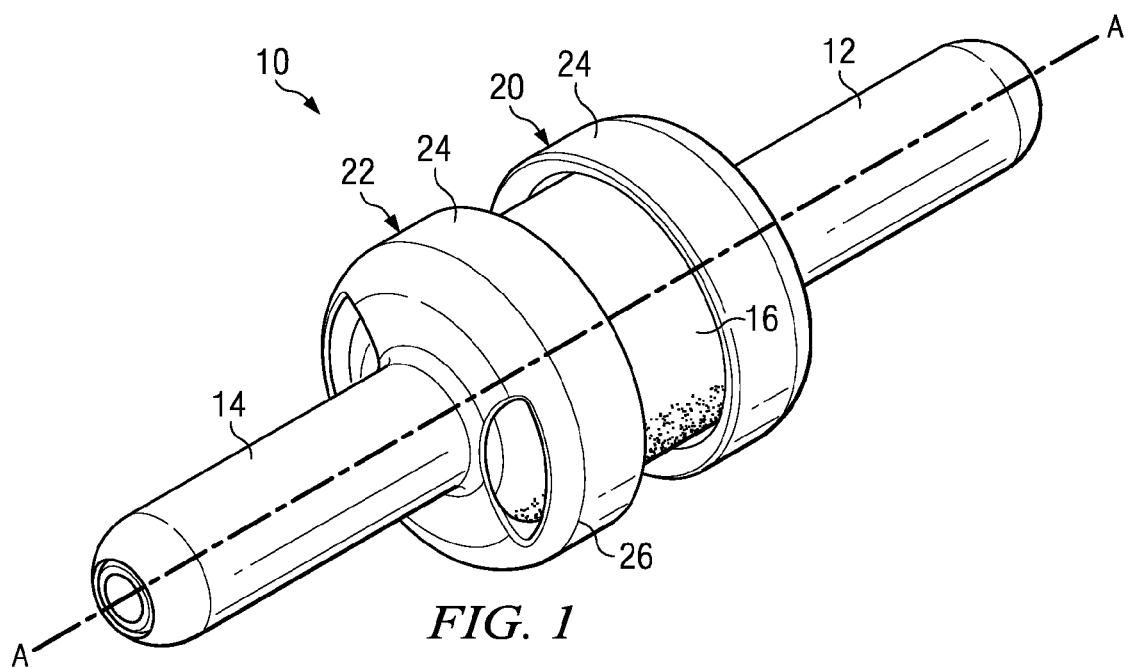
FIG. 1 is a perspective view of an elongated connecting element according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Alterations and further modifications in the illustrated devices, as well as further applications of the principles of the invention as illustrated herein, are contemplated as would normally occur to one skilled in the art to which the invention relates.

Systems and devices for providing dynamic stabilization of one or more spinal motion segments are provided. The systems and devices include a connecting element between two or more bone anchor assemblies that can be attached to at least two or more vertebral bodies of a spinal motion segment. The connecting element extends along a longitudinal axis and includes opposing end members with rod portions at each end engageable to respective ones of the anchor assemblies and a resilient intermediate element between the end members that allows movement of the vertebrae to which the connecting element is attached. The end members can be configured to interfit with the resilient intermediate element to provide a stabilization construct that is movable in response to at least spinal extension, spinal flexion and lateral bending of the spinal column. The resilient intermediate element, or bumper assembly, defines multiple planes and locations of motion relative to the longitudinal axis of the connecting element while providing appropriate stiffness and shear resistance for spinal stabilization as the spinal motion segment deviates from the neutral position.

The anchor assemblies discussed herein can be multi-axial or uni-axial in form, and can include an anchor member engageable to a vertebral body and a receiver, post or other device for receiving or engaging a respective end member of the connecting element. The multi-axial anchor assemblies allow the anchor member to be positioned at various angles relative to the connecting element engaging portion of the anchor assembly. The uni-axial anchor assemblies can also provide a fixed positioning of the connecting element engaging portion to the anchor member. The anchor member of the anchor assemblies can form a distal lower portion that is engageable to a vertebral body with the proximal connecting element engaging portion positioned adjacent the vertebral body. In one embodiment, the anchor member is in the form of a bone screw with a threaded shaft and a proximal head that is pivotally captured in the receiver. In other embodiments, the distal anchor member can be in the form of a hook, staple, cable, tether, suture anchor, interbody fusion implant, artificial disc implant, bolt, or other structure engageable to bony tissue. The implant engaging portion can include a receiver with a U-shape, O-shape, or other shape that defines a passage that receives the respective end member of the connecting element therein, thereon, therethrough, or thereover, for example. The connecting element can extend from one or both of the anchor assemblies for securement to one or more additional vertebral bodies.

FIG. 1 illustrates an elongated connecting element 10 with a first end member 12 and a second end member 14. The first end member 12 and the second end member 14 are preferably substantially aligned along a longitudinal axis A. A resilient intermediate element 16 is present between the first end member 12 and the second end member 14. A flexible tether 18, illustrated in FIGS. 2 and 3, extends between the first end member 12 and the second end member 14 and through the resilient intermediate element 16. The first end member 12 and the second end member 14 are configured to engage the resilient intermediate element 16 when a shear force is applied to the elongated connecting member 10 to dampen radial displacement of the resilient intermediate element 16 and, particularly, the flexible tether 18 by dispersing at least part of the applied shear force into the resilient intermediate element 16.

For the purposes herein, a "shear" force is a force with a component vector that is perpendicular to the longitudinal axis A.

This engagement of the resilient intermediate member 16, minimizes even the possibility that radial displacement of the first end member 12 with respect to the second end member 14 would have the effect that the flexible tether 18 contacts and rubs against the interior of the first and/or second end member 12, 14 upon application of a shear force to the connecting member 10. By dispersing at least part of the applied shear force into the resilient intermediate element 16, the radial displacement of the end members 12, 14, the resilient intermediate element 16, and the flexible tether 18 is dampened or minimized and the chances are reduced that the flexible tether 18 would contact and possibly abrade against the interior of the first and/or second end member 12, 14.

In one embodiment, the first end member 12 includes a first flange 20 and the second end member 14 includes a second flange 22. The first flange 20 and the second flange 22 each include a cylindrical wall 24 extending substantially perpendicularly to the flange 12, 14, and substantially in the direction of the longitudinal axis A, from the perimeter 26 of the first flange 20 and the second flange 22. This creates a cup shape associated with each of first end member 12 and second end member 14.

The resilient intermediate element 16 is disposed within the cup shape formed by the cylindrical walls 24 extending from first flange 18 and second flange 20, as illustrated in FIG. 1. The cylindrical wall 24 of the first flange 18 and second flange 20 are configured to engage the resilient intermediate element 16 upon application of a shear force to the elongated connecting member 10 to disperse at least part of the applied shear force into the resilient intermediate element 16 to minimize the radial displacement of the end members 12, 14, the resilient intermediate element 16, and the flexible tether 18, as described above.

Figure 2:
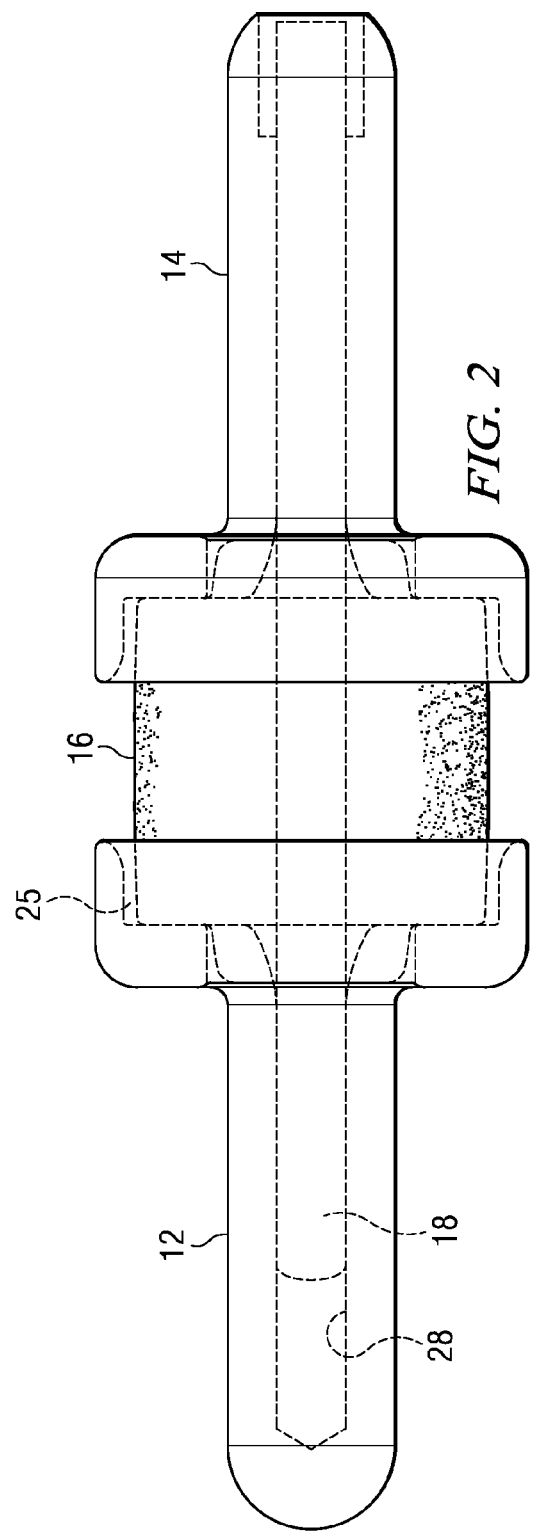
FIG. 2 is a cross-sectional perspective view of the elongated connecting element of FIG. 1.
Figure 3:
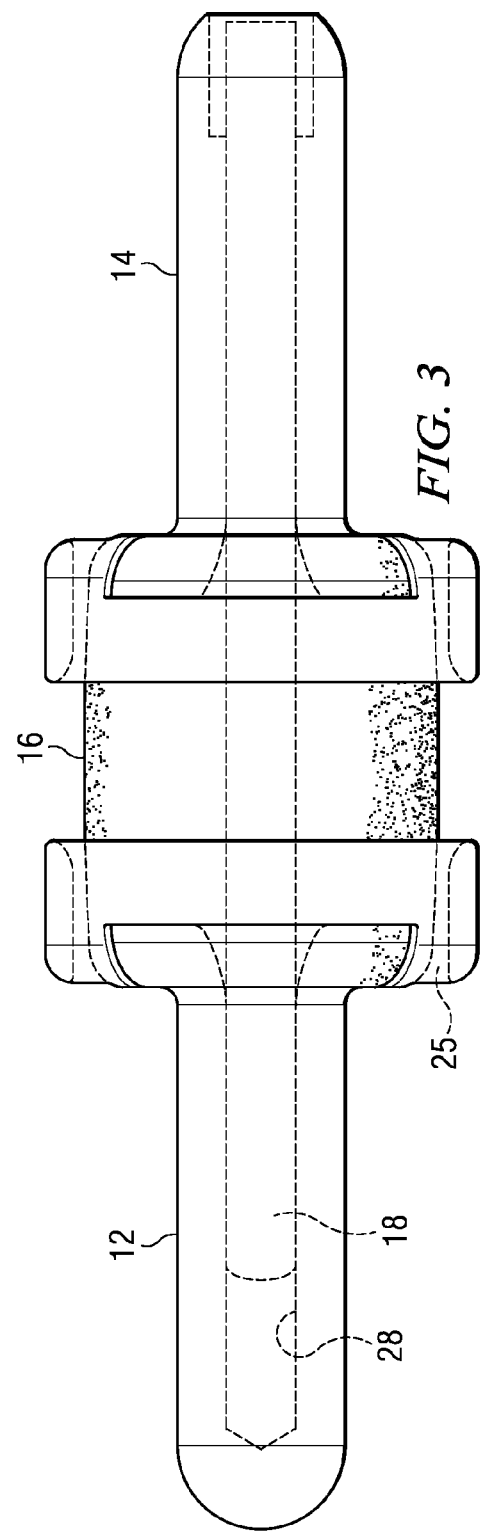
FIG. 3 is another cross-sectional perspective view of the elongated connecting element of FIG. 1.
Figure 6:
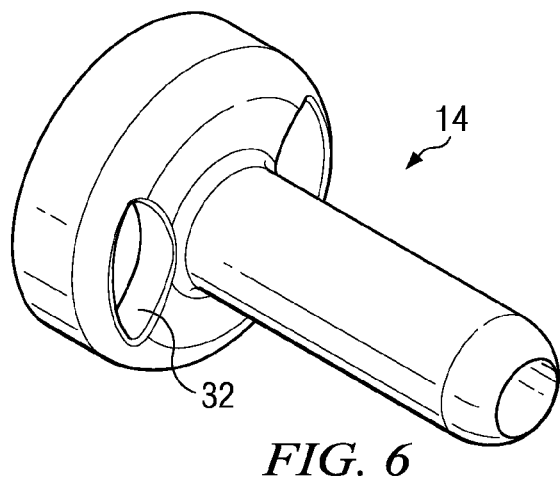
FIG. 6 is another perspective view of an end member of the elongated connecting element of FIG. 1.
Figure 7:
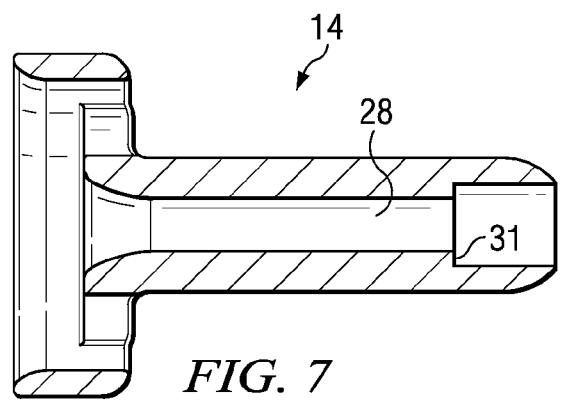
FIG. 7 is another cross-sectional view of an end member of the elongated connecting element of FIG. 1.
Figure 8:
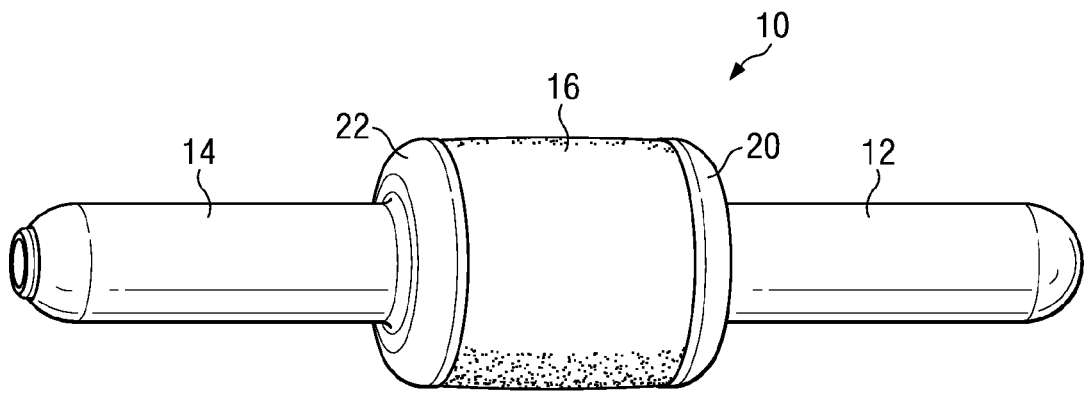
FIG. 8 is a perspective view of an elongated connecting element according to one embodiment of the present invention.
Figure 11:
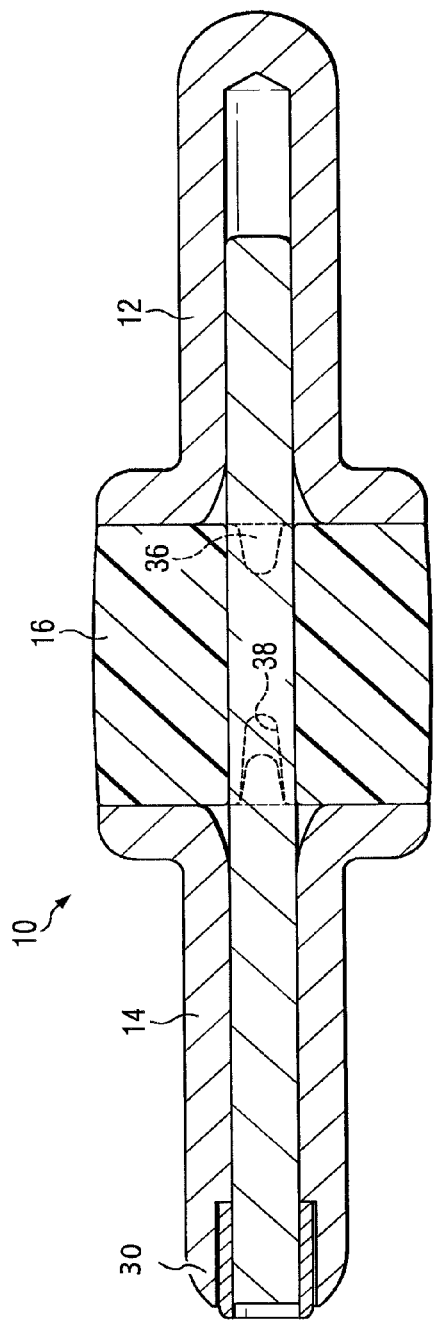
FIG. 11 is another cross-sectional view of the elongated connecting element embodiment of FIG. 8.
Figure 14:
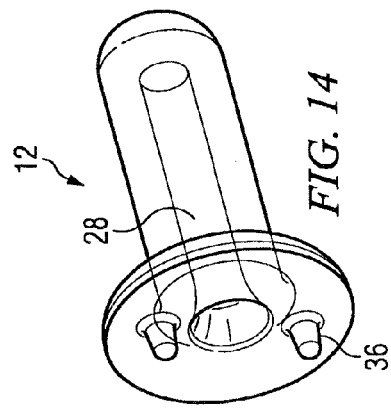
FIG. 14 is a phantom perspective view of an end member of the elongated connecting element embodiment of FIG. 8.

FIGS. 2 and 3 illustrate a cross section of a connecting element in accordance with the present invention, with the first and second end members 12, 14, the flexible intermediate element 16, and the flexible tether 18. Also illustrated in FIGS. 2 and 3 is a bore 28 present in the first end member 12 and the second end member 14. The flexible tether, or coupling member, 18 is disposed in the bore 28 substantially as described in U.S. Ser. No. 11/028,999, filed Jan. 4, 2005, which is incorporated herein by reference in its entirety. This includes stop member or ferrule 30 that is secured to the flexible tether 18 and limits the separation of the first end member 12 and the second end member 14, such as during spinal flexion. Likewise, the resilient intermediate member 16 is also disposed and arranged substantially as described in U.S. Ser. No. 11/028,999.

FIGS. 2 and 3 illustrate a gap 25, showing that the resilient intermediate member 16 need not directly contact the cylindrical walls 24 in the absence of application of a shear force.

FIGS. 4, 5, 6, and 7 illustrate second end member 14. Second end member 14 includes stop member seat 31 and at least one aperture 32. Stop member seat 31 provides a seat for stop member 30 when the first end member 12 and the second end member 14 are urged away from each other, such as during spinal flexion. As illustrated, there are two apertures 32, evenly spaced about the longitudinal axis A. The apertures maintain rotational alignment (about axis A) of end members 12 and 14 by being configured to accept a portion of the resilient intermediate member 16.

Figure 4:
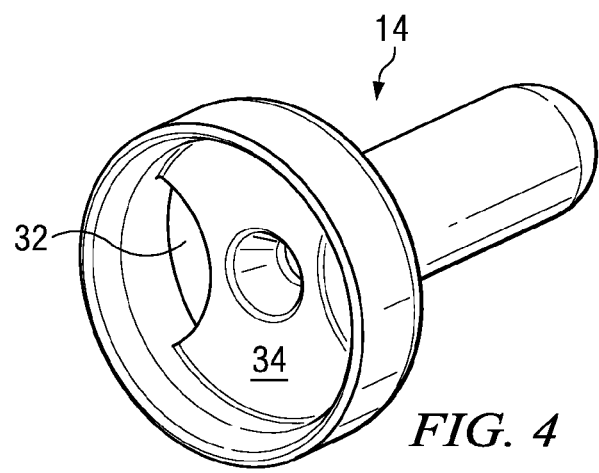
FIG. 4 is a perspective view of an end member of the elongated connecting element of FIG. 1.
Figure 5:
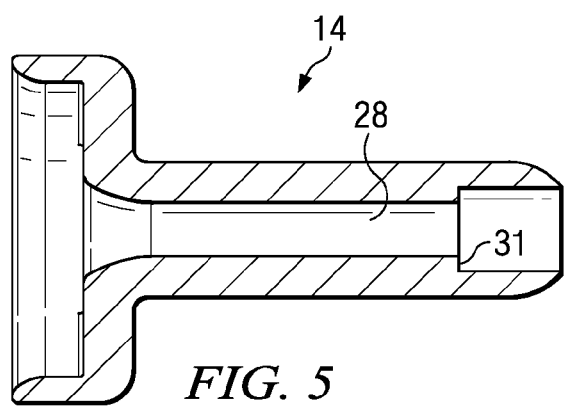
FIG. 5 is a cross-sectional view of an end member of the elongated connecting element of FIG. 1.

As seen in FIG. 4, first flange 20 includes an inner face 34. In some embodiments, the flange inner face 34 engages the resilient intermediate element 16 in the neutral position of connecting element 10, due to the preload applied during assembly of element 10. The preload applied during assembly may vary, and in some embodiments, the inner face 34 does not engage the resilient intermediate element 16 in the neutral position of connecting element 10.

When the first end member 12 and the second end member 14 are moved toward each other, such as during extension of the spine when the connecting element 10 is attached along a spinal column, the flange inner face 34 engages the resilient intermediate element 16 to apply or increase, depending on whether a preload force is already applied, a longitudinal force to the resilient intermediate member 16. The resilient intermediate member 16 then deforms and absorbs at least part of the applied force, and dampens the movement of the first end member 12 and the second end member 14 toward each other. The flexible tether 18 slides within the bore 28, illustrated in FIGS. 5 and 7.

FIGS. 8 through 15 illustrate an embodiment in accordance with the present invention in which the first flange 20 and the second flange 22 include at least one protuberance 36. The resilient intermediate element 16 includes a plurality of indentations 38. The indentations 38 are configured to cooperate with the protuberances 36. As illustrated, the protuberances 36 fit within the indentations 38. Upon application of a shear force to the connecting element 10, the protuberances 36 exert force against the sides of the indentations 38 to disperse at least part of the applied shear force into the resilient intermediate element 16, which in turn minimizes or dampens the radial displacement of the end members 12, 14, the resilient intermediate element 16, and the flexible tether 18 and the chances are reduced that the flexible tether 18 will contact and abrade against the interior of the first and/or second end member 12, 14.

In some embodiments, the protuberances 36 also will assist maintenance of rotational alignment about longitudinal axis A of end members 12, 14.

As illustrated in FIGS. 9 and 10, the depth of some indentations 38 is greater than the height of the protuberances 36. This enables the first end member 12 and the second end member 14 to be displaced toward each other, such as during extension of the spine when the connecting element is attached along a spinal column, as discussed above. The protuberances 36 are selected according to criteria selected by the user and may be of any shape, size, etc. They may be rounded or squared, tapered or spiked, and may be a boss, stub, nub, stud, knob, or the like. Likewise, the shape of the indentations may be selected based on criteria selected by the user and configured to cooperate as described with the protuberances.

Figure 13:
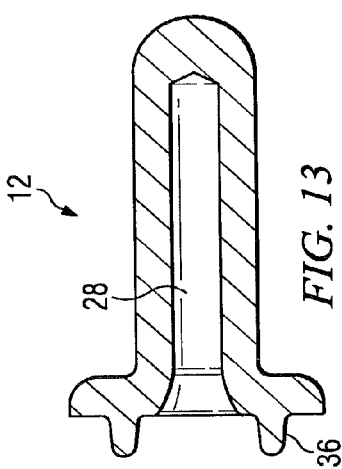
FIG. 13 is a cross-sectional view of an end member of the elongated connecting element embodiment of FIG. 8.
Figure 12:
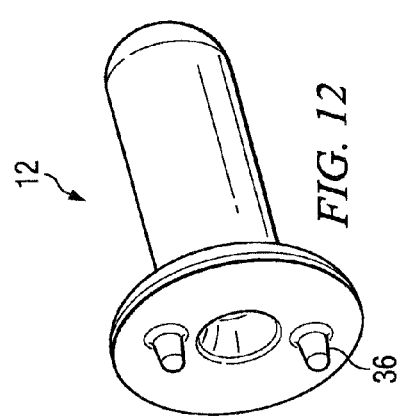
FIG. 12 is a perspective view of an end member of the elongated connecting element embodiment of FIG. 8.
Figure 15:
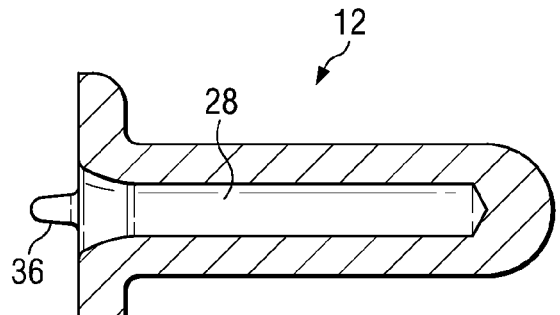
FIG. 15 is another cross-sectional view of an end member of the elongated connecting element embodiment of FIG. 8

FIGS. 12 through 15 illustrate an embodiment of first end member 12. FIG. 13 illustrates a cross section of the first end member 12 through a plane passing through at least one protuberance 36. FIG. 15 illustrates a cross section of first end member 12 through a plane that does not pass through at least one protuberance 36.

Figure 16:
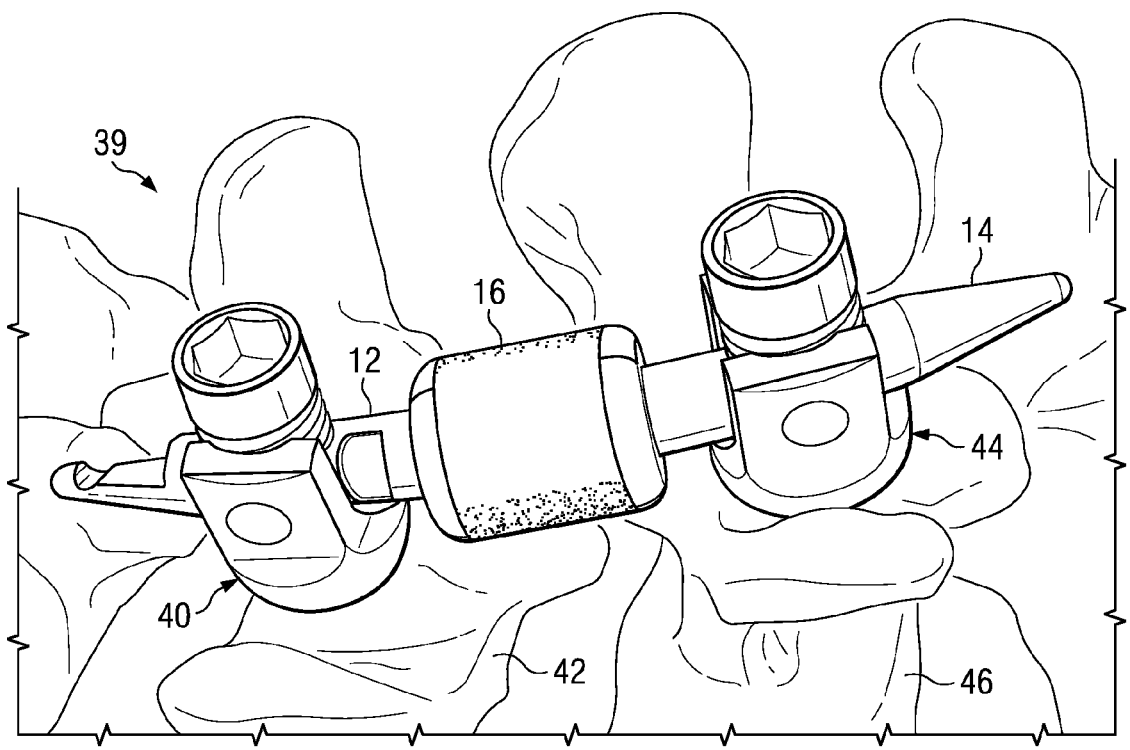
FIG. 16 is a perspective view of an embodiment of an elongated connecting element and system for stabilizing a first vertebra with respect to a second vertebra according to one embodiment of the present invention.

FIG. 16 illustrates a system 39 for stabilizing a first vertebra or vertebral body with respect to a second vertebra or vertebral body in which a first anchor assembly 40 is attached to a first vertebra 42 and a second anchor assembly 44 is attached to a second vertebra 46. The stabilization system 39 is configured for attachment to a first vertebra 42 and a second vertebra 46, but it is to be noted that the invention includes such a system that is not attached to the first and second vertebra 42, 46. As described above, the anchor assemblies 40, 44 included herein can be multi-axial or uni-axial in form, and can include an anchor member attachable to a vertebral body and a receiver, post or other device for receiving or engaging a respective end member of the connecting element.

First end member 12 is configured to engage with first anchor assembly 40 and second end member 14 is configured to engage with second anchor assembly 44. In this way, the elongated connecting element 10 is configured to be attached to and to stabilize a first vertebra 42 and a second vertebra 46.

Figure 17:
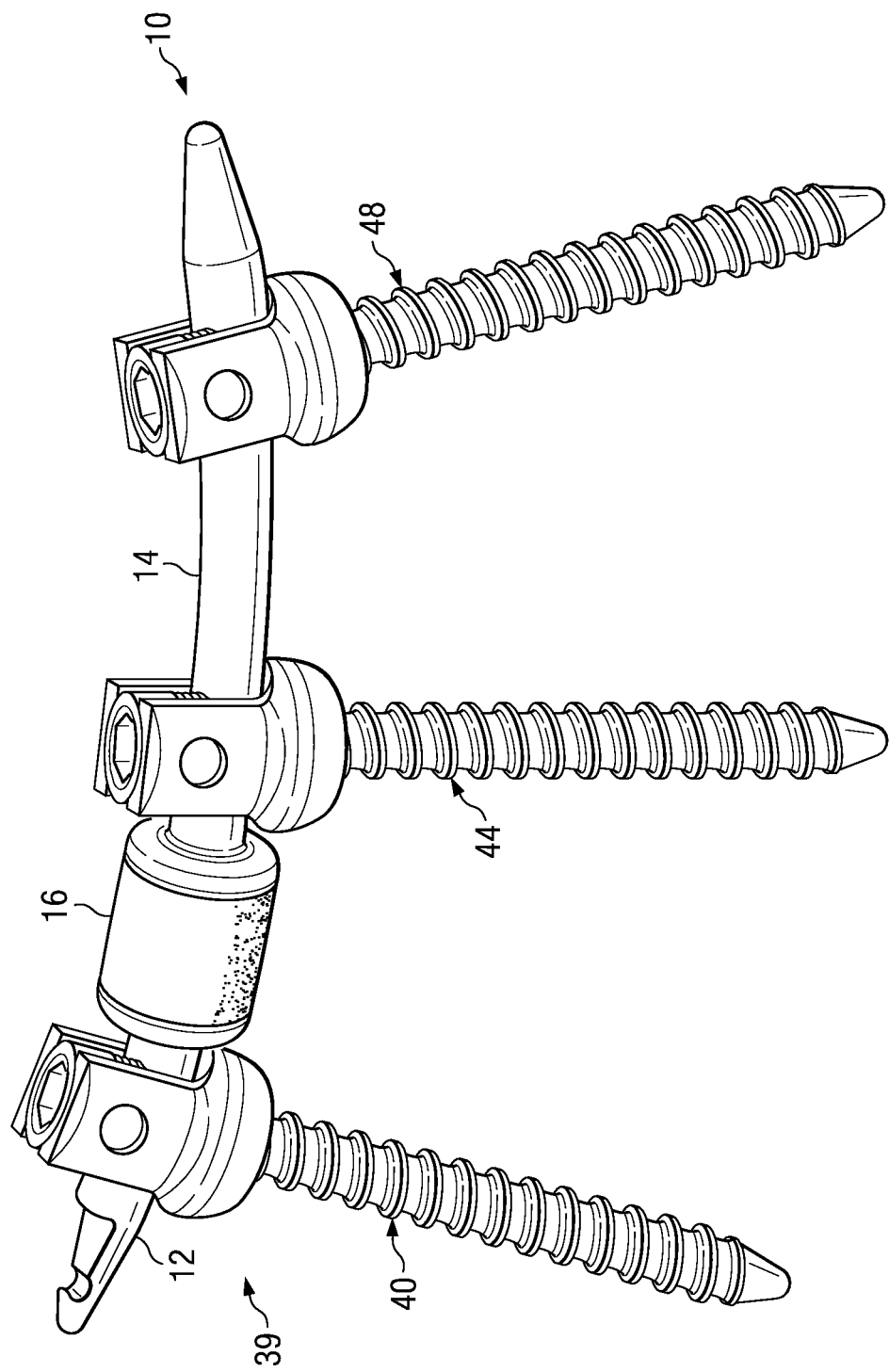
FIG. 17 a perspective view of an embodiment of an elongated connecting element and system for stabilizing a first vertebra with respect to a second vertebra according to one embodiment of the present invention.

FIG. 17 illustrates an embodiment of the stabilization system 39 having a third anchor assembly 48 that can be used to anchor to a third vertebra or vertebral body. In this embodiment, the second end member 14 is elongated and is anchored to both the second anchor assembly 44 and the third anchor assembly 48. This provides for stabilization of three adjacent vertebrae. The system 39 may also stabilize three adjacent vertebra without having the second anchor assembly 44, in which case the connecting element will be engaged between non-adjacent vertebrae to which the first anchor assembly 40 and the third anchor assembly 48 are attached. In this manner, the connecting member 10 may be used to stabilize any number of vertebral bodies by attachment to adjacent or non-adjacent vertebrae.

In yet another embodiment, the elongated connecting member may include a second resilient intermediate member 16 disposed between the second anchor assembly 44 and the third anchor assembly 48. In this manner, there may be any number of resilient intermediate elements between any number of adjacent or non-adjacent vertebrae.

In a further embodiment, the flanges 20, 22 each include a cylindrical wall 24 forming a cup shape, as described above, in combination with the flanges 20, 22 each including at least one protuberance 36 designed to cooperate with corresponding indentations 38 in the resilient intermediate element 16. In this embodiment, the resilient intermediate element both fits into the cup shape of the first end member 12 and the second end member 14 and further includes indentations 38 to cooperate with corresponding protuberances 36 from the flanges 20, 22.

The form, shape, and the material of construction of the end members 12, 14, the resilient intermediate element 16, and the flexible tether 18 can be selected based on criteria chosen by the user without departing from the spirit or scope of the invention. Some suitable materials are included in U.S. Ser. No. 11/028,999. For example, the flexible tether may be wire, rope, cord, band, belt, suture, bar, cable, rod, mesh, fabric, or other suitable form and may be a metal cable, such as a titanium or titanium alloy cable. The end members 12, 14 also may be made of metal, such as titanium. Resilient intermediate element 16 may be of any shape, such as cylindrical or prismatic, including rectangular, pentagonal, hexagonal, etc. prisms, and may be made from various materials such as polyurethane or polycarbonate urethane, and may be made from a resorbable material.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

We claim:

1. A system for stabilizing a first vertebra with respect to a second vertebra, comprising:
   a. first and second anchor assemblies attachable to the first vertebra and the second vertebra, respectively;
   b. an elongated connecting element comprising:
      i. a first end member configured to engage with the first anchor assembly and a second end member configured to engage with the second anchor assembly, the first end member including an inner surface defining a first bore and the second end member including an inner surface defining a second bore, the first end member and the second end member substantially aligned along a longitudinal axis;
      ii. a resilient intermediate element positioned between the first end member and the second end member having an inner surface defining a third bore that is communication with the first and second bores; and
      iii. a flexible tether disposed in the bores;
   wherein the first end member comprises a first flange having at least one protuberance, the second end member comprises a second flange having at least one protuberance, and the resilient intermediate element including first and second axial ends and comprising a plurality of indentations configured to cooperate with the protuberances of the first flange and the second flange, each of the plurality of indentations extending inward from one of the axial ends and including an open end and an opposing closed end with the open end positioned farther from a longitudinal center of the resilient intermediate element, wherein a depth of the indentations is greater than a height of the protuberances of the first and second flange such that a distal surface of at least one of the protuberances is spaced apart from a bottom surface of a respective indentation when a respective protuberance is disposed in a respective indentation; and
   wherein the first end member and the second end member each engage the resilient intermediate element to dampen radial displacement of the resilient intermediate element with respect to the longitudinal axis when shear force is applied to the elongated connecting element.

2. The system of claim 1, wherein the first and second anchor assemblies are bone screws.

3. The system of claim 2, wherein the first and second anchor assemblies are multi-axial bone screws.

4. The system of claim 1, wherein the first end member comprises a first cup-shaped flange, the second end member comprises a second cup-shaped flange, and the resilient intermediate element is positioned within and between the first cup-shaped flange and the second cup-shaped flange.

5. The system of claim 1, wherein the first vertebra and the second vertebra are non-adjacent.

6. The system of claim 1, further comprising a third anchor assembly attachable to a third vertebra.

7. The system of claim 1, wherein the elongated connecting element includes a stop member engaged with the flexible tether configured to limit separation of the first end member from the second end member.

8. The system of claim 1, wherein the second bore includes an enlarged portion defining a stop member seat and the elongated connecting element includes a stop member engaged with the flexible tether configured for disposal in the stop member seat to limit separation of the first end member from the second end member.

9. The system of claim 1, wherein the first end surface includes an aperture extending through inner and outer surfaces of the first end surface configured for disposal of the resilient intermediate element when the resilient intermediate element is positioned between the first end member and the second end member.

10. The system of claim 1, wherein the first end surface includes a pair of spaced apart apertures each extending through inner and outer surfaces of the first end surface configured for disposal of the resilient intermediate element when the resilient intermediate element is positioned between the first end member and the second end member.

11. The system of claim 1, further comprising a third anchor assembly attachable to a third vertebra, the first, second and third anchor assemblies each including an inner surface defining a U-shaped cavity, wherein the second end member is disposed in the U-shaped cavity of the first anchor assembly and the first anchor member is disposed in the U-shaped cavities of the second and third anchor assemblies.

12. The system of claim 1, wherein the first bore includes a first end adjacent the first end surface and a second end adjacent the second end surface, the first bore being tapered between the first and second ends thereof.

13. The system of claim 1, wherein:
   the first end member extends along a longitudinal axis between the first and second end surfaces;
   the first flange extends transverse to the longitudinal axis and includes a lateral surface extending parallel with the longitudinal axis; and
   the at least one protuberance on the first flange is spaced apart from the lateral surface.

14. The system of claim 1, wherein:
   the first end member extends along a longitudinal axis between the first and second end surfaces;
   the first bore includes a transverse face adjacent the second end surface extending transverse to the longitudinal axis; and
   a first end of the flexible tether is disposed in the first bore and an opposite second end of the flexible tether is disposed in the second bore such that an end face defined by the first end of the flexible tether is spaced apart from the transverse face.

15. The system of claim 1, wherein the first and second end members and the flexible tether comprise titanium and the resilient intermediate member comprises polyurethane.

16. The system of claim 1, wherein the first and second end members and the flexible tether comprise titanium and the resilient intermediate member comprises polycarbonate urethane.

17. The system of claim 1, wherein the first and second end members and the flexible tether comprise titanium and the resilient intermediate member comprises a resorbable material.

18. The system of claim 1, wherein the first and second end members and the flexible tether comprise a titanium alloy and the resilient intermediate member comprises a resorbable material.

19. An elongated connecting element for stabilizing a first vertebra with respect to a second vertebra, the elongated connecting element comprising:
   a. a first rigid end member and a second rigid end member substantially aligned along a longitudinal axis, the first end member including an inner surface defining a first bore and the second end member including an inner surface defining a second bore;
   b. a first cup-shaped member that includes a first flange and an outwardly-extending first sidewall that are associated with the first rigid end member and a second cup-shaped member that includes a second flange and an outwardly-extending second sidewall that are associated with the second rigid end member;
   c. a resilient intermediate element positioned within and between the first cup-shaped member and the second cup-shaped member, the intermediate element including an inner surface defining a third bore in communication with the first and second bores; and
   d. a flexible titanium tether disposed in the bores;
   e. a first plurality of protuberances that extend outward from the first flange and are spaced radially away from the first sidewall and a second plurality of protuberances that extend outward from the second flange and are spaced radially away from the second sidewall, each of the plurality of protuberances including an elongated shape with an exposed tip that faces towards a longitudinal center of the resilient intermediate element;
   f. a plurality of indentations disposed on the resilient intermediate member with inlets positioned on axial ends of the resilient intermediate member and configured to cooperate with the protuberances of the first flange and the second flange, the resilient intermediate element positioned between the first flange and the second flange, wherein a depth of the indentations is greater than a height of the protuberances of the first and second flange such that a distal surface of at least one of the protuberances is spaced apart from a bottom surface of a respective indentation when a respective protuberance is disposed in a respective indentation;
   wherein the first cup-shaped member flange of the first end member and the second cup-shaped member flange of the second end member each engage the resilient intermediate element to dampen radial displacement of the resilient intermediate element with respect to the longitudinal axis when shear force is applied to the elongated connecting element.

20. An elongated connecting element for stabilizing a first vertebra with respect to a second vertebra, the elongated connecting element comprising:
   a. a first rigid end member and a second rigid end member substantially aligned along a longitudinal axis, the first end member including an inner surface defining a first bore and the second end member including an inner surface defining a second bore;
   b. a first flange having at least one protuberance and associated with the first rigid end member, and a second flange having at least one protuberance and associated with the second rigid end member;
   c. a resilient intermediate element having a plurality of indentations each with inlets positioned on axial ends and configured to cooperate with the protuberances of the first flange and the second flange, the resilient intermediate element positioned between the first flange and the second flange, the intermediate element including an inner surface defining a third bore in communication with the first and second bores, wherein a depth of the indentations is greater than a height of the protuberances of the first and second flange such that a distal surface of at least one of the protuberances is spaced apart from a bottom surface of a respective indentation when a respective protuberance is disposed in a respective indentation; and
   d. a flexible titanium tether disposed in the bores;
   wherein each of the protuberances including an exposed tip that faces towards a longitudinal center of the resilient intermediate element; and wherein the protuberances of the first flange and the second flange engage the indentations of the resilient intermediate element to dampen radial displacement of the resilient intermediate element with respect to the longitudinal axis when shear force is applied to the elongated connecting element.

* * * * *